(12) United States Patent
Singh (10) Patent No.: US 10,709,621 B2
(45) Date of Patent: Jul. 14, 2020

(54) CHOKING PROOF PEEL RESISTANT ADHESIVE BANDAGES PLACED ON BABIES AFTER BLOOD TESTS OR VACCINATIONS

(71) Applicant: Sanjeev Kumar Singh, Alpharetta, GA (US)

(72) Inventor: Sanjeev Kumar Singh, Alpharetta, GA (US)

(*) Notice: Subject to any disclaimer, the term of this patent is extended or adjusted under 35 U.S.C. 154(b) by 489 days.

(21) Appl. No.: 15/601,242

(22) Filed: May 22, 2017

(65) Prior Publication Data

US 2018/0333315 A1 Nov. 22, 2018

(51) Int. Cl.
  *A61F 15/00* (2006.01)
  *A61F 13/00* (2006.01)
  *A61F 13/02* (2006.01)
  *A61F 13/10* (2006.01)

(52) U.S. Cl.
  CPC ...... *A61F 15/006* (2013.01); *A61F 13/00063* (2013.01); *A61F 13/00085* (2013.01); *A61F 13/02* (2013.01); *A61F 13/0203* (2013.01); *A61F 13/0246* (2013.01); *A61F 13/10* (2013.01); *A61F 2013/00297* (2013.01); *A61F 2013/00553* (2013.01); *A61F 2013/00646* (2013.01); *A61F 2013/00655* (2013.01); *A61F 2013/00719* (2013.01); *A61F 2013/00808* (2013.01)

(58) Field of Classification Search
  CPC .............. A61F 15/006; A61F 13/00063; A61F 13/00085; A61F 13/02; A61F 13/0203; A61F 13/0246; A61F 2013/00553; A61F 2013/00646; A61F 2013/00655; A61F 2013/00719; A61F 2013/00808; A61F 13/10
  USPC ..................... 602/41–44, 48, 52, 54, 56, 58; 128/888–894; D24/189
  See application file for complete search history.

(56) References Cited

U.S. PATENT DOCUMENTS

| 2,875,758 A | * | 3/1959 | Fuzak | A61F 13/105 602/58 |
| 3,989,041 A | * | 11/1976 | Davies | A61F 13/108 602/62 |
| 4,345,590 A | * | 8/1982 | Nakajima | A61F 13/066 602/65 |

(Continued)

*Primary Examiner* — Anna K Kinsaul
*Assistant Examiner* — Caitlin A Carreiro
(74) *Attorney, Agent, or Firm* — Sanjeev K. Singh (57) ABSTRACT

An adhesive bandage is provided which has at least four arms instead of standard two where two of which being of a different length than other two to resist its removal from skin by a baby. The adhesive bandage includes a first and a second bandage arms and a third and a fourth bandage arms. The first and second bandage arms are transverse to the third and fourth bandage arms. The first and second bandage arms are longer in length to the third and fourth bandage arms. The adhesive bandage further includes a medicated pad at an intersection of the first and second bandage arms and the third and fourth bandage arms. In one embodiment, the new bandage includes an adhesive strip and a clip such that the adhesive strip is looped through the clip. In another embodiment, the new bandage includes an adhesive strip and a Velcro strap such that the adhesive strip is looped through the Velcro strap.

10 Claims, 4 Drawing Sheets

(56) References Cited

U.S. PATENT DOCUMENTS

| | | | |
|---|---|---|---|
| 8,742,196 B2* | 6/2014 | Arbesman | A61F 5/0106 602/54 |
| 2010/0106120 A1* | 4/2010 | Holm | A61F 13/068 604/358 |

* cited by examiner

CHOKING PROOF PEEL RESISTANT ADHESIVE BANDAGES PLACED ON BABIES AFTER BLOOD TESTS OR VACCINATIONS

BACKGROUND

1. Field

Aspects of the present invention relates to adhesive bandages commonly used for babies, and more particularly, choking proof and peel resistant adhesive bandages which form a ring-like grip that keeps the choking proof adhesive bandage in place despite any attempt to take it off by a baby.

2. Description of the Related Art

A breathing emergency is any respiratory problem that can threaten a person's life and choking is an example of breathing emergencies. Choking is a common breathing emergency. It occurs when the person's airway is partially or completely blocked. If a conscious person is choking, his or her airway has been blocked by a foreign object, such as a piece of food or a small toy; by swelling in the mouth or throat; or by fluids, such as vomit or blood. With a partially blocked airway, the person usually can breathe with some trouble. A person with a partially blocked airway may be able to get enough air in and out of the lungs to cough or to make wheezing sounds. The person also may get enough air to speak. A person whose airway is completely blocked cannot cough, speak, cry or breathe at all.

Choking is a common cause of injury and death in children younger than 5 years. Because young children put nearly everything in their mouths, small, nonfood items, such as safety pins, small parts from toys and coins, often cause choking. However, food is responsible for most of the choking incidents in children. Since choking remains a significant danger to children younger than 5 years, the American Academy of Pediatrics (AAP) further recommends keeping the following foods, and other items meant to be chewed or swallowed, away from young children.

For prevention, do not give young children round, firm foods such as hot dogs and carrot sticks unless chopped into pieces ½ inch or smaller. Keep small objects such as safety pins, small parts from toys and coins away from small children. Make sure that toys are too large to be swallowed. Make sure that toys have no small parts that could be pulled off. If you are unsure whether an object is safe for young children, test it by trying to pass it through a toilet paper roll. If it fits through the 1¾-inch diameter roll, it is not safe for young children.

Although food items cause most of the choking injuries in children, toys and household items also can be hazardous. Balloons, when broken or un-inflated, can choke or suffocate young children who try to swallow them. According to the Consumer Product Safety Commission (CPSC), more children have suffocated on non-inflated balloons and pieces of broken balloons than any other type of toy.

Signals of choking include: coughing, either forcefully or weakly, clutching the throat with one or both hands, inability to cough, speak, cry or breathe, making high-pitched noises while inhaling or noisy breathing, panic, bluish skin color, and losing consciousness if blockage is not removed.

A bandage is a piece of material used either to support a medical device such as a dressing or splint, or on its own to provide support to or to restrict the movement of a part of the body. Bandages pose a choking threat. Use of bandages on children younger than 2 years of age presents a possible choking hazard. Often, bandages are placed on the fingers and hands of young children after routine blood tests or vaccinations. Inevitably, the bandaged hand or finger goes into the child's mouth, creating the potential to choke. Doctors always caution parents to closely supervise children who are wearing such bandages, and tell them to remove bandages promptly once bleeding has stopped.

Therefore, an adhesive bandage for babies overcoming various problems and shortcomings of the prior art would be an important improvement in the art.

SUMMARY

Briefly described, aspects of the present invention relate to choking proof and peel resistant bandages with a combination of a standard bandage and two transverse longer bandage strips which form a ring that keeps the choking proof bandage in place even if it is tampered with by a baby to take it off from their skin. By being impossible to be removed from the skin such as a hand, a finger or an arm due to extra bandage area of adhesion available from the two transverse longer bandage strips the choking proof bandage almost eliminates the potential to choke in babies.

In accordance with one illustrative embodiment of the present invention, an adhesive bandage is provided. The adhesive bandage includes a first and a second bandage arms and a third and a fourth bandage arms. The first and second bandage arms are transverse to the third and fourth bandage arms. The first and second bandage arms are longer in length to the third and fourth bandage arms. The adhesive bandage further includes a medicated pad at an intersection of the first and second bandage arms and the third and fourth bandage arms.

Consistent with another embodiment, an adhesive bandage is provided. The adhesive bandage includes a bandage strip with a channel in a middle portion to thread through an object. The adhesive bandage further includes a clip threaded through the channel of the bandage strip. The clip is configured to be placed on an arm or a thigh of a baby. The adhesive bandage further includes a medicated pad at an intersection of the middle portion of the bandage strip and the clip.

Consistent with yet another embodiment, an adhesive bandage is provided. The adhesive bandage includes a bandage strip with a channel in a middle portion to thread through an object. The adhesive bandage further includes a Velcro band threaded through the channel of the bandage strip. The Velcro band is configured to be placed on an arm or a thigh of a baby. The adhesive bandage further includes a medicated pad at an intersection of the middle portion of the bandage strip and the Velcro band.

DETAILED DESCRIPTION

To facilitate an understanding of embodiments, principles, and features of the present invention, they are explained hereinafter with reference to implementation in illustrative embodiments. In particular, they are described in the context of a choking proof bandage capable of staying in place when applied on the skin of babies such as younger than 2 years. Embodiments of the present invention, however, are not limited to use in the described devices or methods.

The components and materials described hereinafter as making up the various embodiments are intended to be illustrative and not restrictive. Many suitable components and materials that would perform the same or a similar function as the materials described herein are intended to be embraced within the scope of embodiments of the present invention.

Although some embodiments of this invention may be described and illustrated herein in terms of two extra transverse longer bandage arms, it should be understood that embodiments of this invention are not so limited, but are generally applicable to any number of arms such as one, two or more arms. Further, although some embodiments of this invention may be described and illustrated herein in the context of a medicated and a sticky bandage, it should be understood that embodiments of this invention are not so limited, but are generally applicable to any number of bandage type arrangement.

Figure 1A:
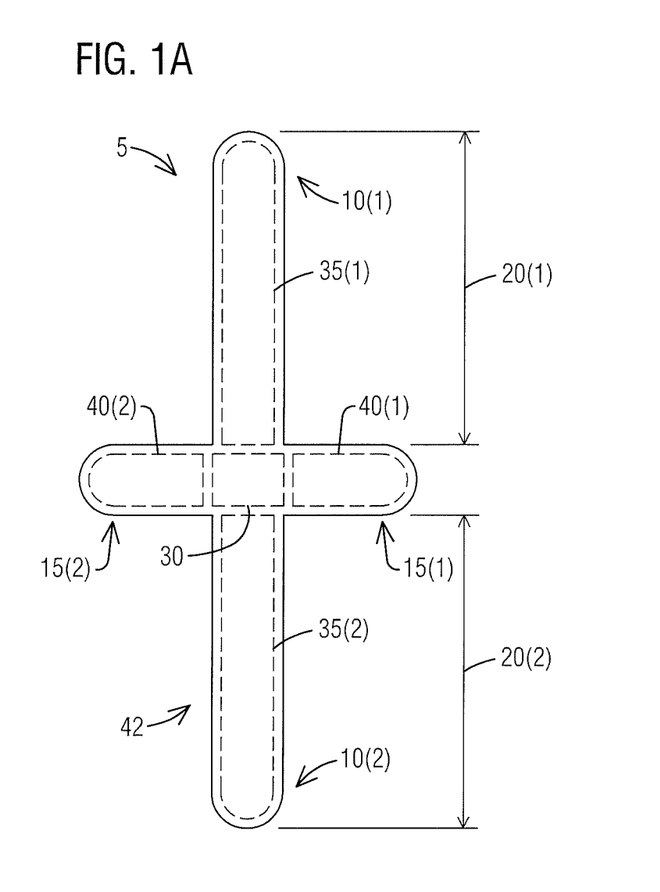
FIG. 1A illustrates a front view of a choking proof bandage including two extra transverse longer bandage in accordance with an exemplary embodiment of the present invention.

FIG. 1A illustrates a front view of a first choking proof bandage 5 including a first and a second transverse longer bandage arms 10(1-2) in accordance with an exemplary embodiment of the present invention. The first choking proof bandage 5 includes a third and a fourth shorter bandage arms 15(1-2). The first and second transverse longer bandage arms 10(1-2) are transverse to the third and fourth shorter bandage arms 15(1-2). For example, they can be at 90 degrees or even less such as 85 degrees or even lesser at about 60 degrees. They can be essentially at any desired angle based on a particular application. The present invention is not limited to any particular angle. The first and second transverse longer bandage arms 10(1-2) may have a first length 20(1-2) each. The third and fourth shorter bandage arms 15(1-2) may have a second length 25(1-2) each. The first length 20(1-2) may be greater than the second length 25(1-2). For example, the first length 20(1-2) may be twice the second length 25(1-2) or more than twice the second length 25(1-2).

However, one skilled in the art would appreciate that they can have any length ratio other than twice based on a particular application. The present invention is not limited to any particular length ratio between two types of bandage arms as long as there is some length differential between the two types of bandage arms.

The first choking proof bandage 5 has a choking proof property by being longer (having relatively more area of an adhesive bond from the first and second transverse longer bandage arms 10(1-2)) than a normal, typical or standard bandage with only the third and fourth shorter bandage arms 15(1-2). The first choking proof bandage 5 has a peel resistant property by having a relative peel resistance of adhesive bonds between separable portions of the first choking proof bandage 5 by means of a tearable pattern of bandage parts that stops the ripping process (not shown as a peel resistant design of an adhesive tape or patch being cut in small separately peelable sections is well known). The peel resistance needed may be determined and set via an adhesive strength of the first choking proof bandage 5 over a specified length of an adhesive bond based on a peel force a 2-3 year old baby can apply to peel the first choking proof bandage 5, e.g., in a longitudinal direction of the first and second transverse longer bandage arms 10(1-2).

In one embodiment, the first choking proof bandage 5 may include a medicated pad 30 at an intersection of the first and second transverse longer bandage arms 10(1-2) and the third and fourth shorter bandage arms 15(1-2). On the side of the medicated pad 30, the first and second transverse longer bandage arms 10(1-2) include a first and a second sticky portions 35(1-2). On the side of the medicated pad 30, the third and fourth shorter bandage arms 15(1-2) include a third and a fourth sticky portions 40(1-2). The first and second sticky portions 35(1-2) and the third and fourth sticky portions 40(1-2) may generally cover the area other than the medicated pad 30 and comprise an adhesive sheet 42. The adhesive sheet 42 is usually a woven fabric, plastic (PVC, polyethylene or polyurethane), or latex strip.

The first and second sticky portions 35(1-2) and the third and fourth sticky portions 40(1-2) make the first choking proof bandage 5 an adhesive bandage. The first and second sticky portions 35(1-2) and the third and fourth sticky portions 40(1-2) may include peel strips (not shown) to preserve the adhesion surface prior to application of the first choking proof bandage 5 on a skin of a baby.

The first choking proof bandage 5 may be a most common type of bandage as the gauze bandage, a simple woven strip of material, or a woven strip of material with a Telfa absorbent barrier to prevent adhering to wounds. The first choking proof bandage 5 may be an adhesive bandage may be a small medical dressing used for injuries not serious enough to require a full-size bandage.

The first choking proof bandage 5 may be an adhesive bandage suitable for placing on the skin after blood tests or vaccinations. An adhesive bandage is a small, flexible sheet of material which is sticky on one side, with a smaller, non-sticky, absorbent medicated pad 30 stuck to the sticky side. The medicated pad 30 is placed against the wound, and overlapping edges of the sticky material are smoothed down so they stick to the surrounding skin. The adhesive bandage protects the wound and scab from friction, bacteria, damage, and dirt. Thus, the healing process of the body is less disturbed. Some of the dressings have antiseptic properties.

In one embodiment, the first and second transverse longer bandage arms 10(1-2) and the third and fourth shorter bandage arms 15(1-2) may be thin strips of bandages. For example, the first and second transverse longer bandage arms 10(1-2) and the third and fourth shorter bandage arms 15(1-2) may have a thickness of 0.5-1 mm. The first choking proof bandage 5 may be adhesive bandages in multiple sizes including waterproof fabric and stretch bandages. The first and second transverse longer bandage arms 10(1-2) may have a first width and the third and fourth shorter bandage arms 15(1-2) may have a second width such that the first width and the second width may be substantially equal.

Figure 1B:
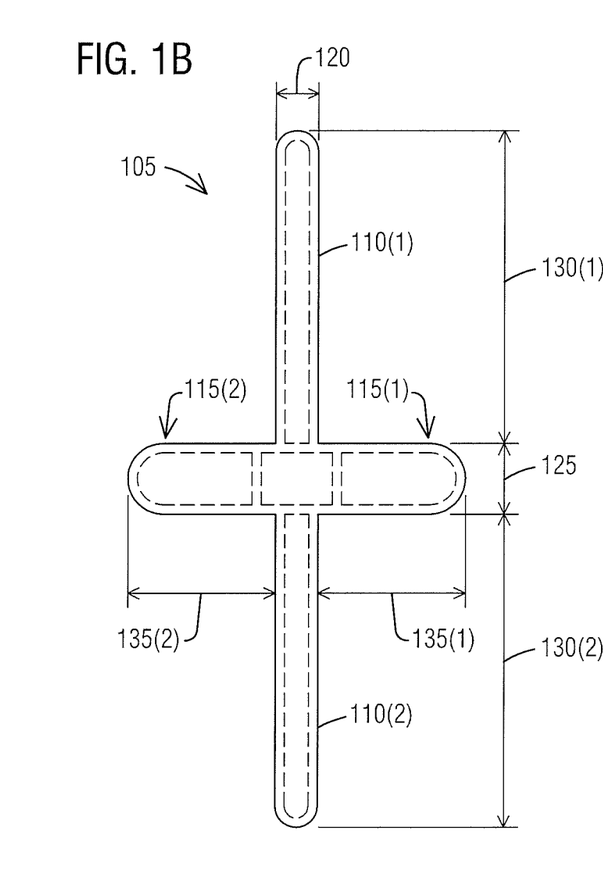
FIG. 1B illustrates a front view of a hybrid choking proof bandage including a first and a second transverse longer bandage arms in accordance with an exemplary embodiment of the present invention.

FIG. 1B illustrates a front view of a hybrid choking proof bandage 105 including a first and a second transverse longer bandage arms 110(1-2) in accordance with an exemplary embodiment of the present invention. The hybrid choking proof bandage 105 includes a third and a fourth shorter bandage arms 115(1-2). The first and second transverse longer bandage arms 110(1-2) may have a first width 120 and the third and fourth shorter bandage arms 115(1-2) may have a second width 125 such that the first width 120 and the second width 125 may be different. In other embodiments, for example, the first width 120 may be less such as about half the second width 125. For example, the hybrid choking proof bandage 105 may be a flexible fabric adhesive bandage with the second width 125 of ¾ inch and the first width 120 being half of ¾ inch. In this way, by being narrow in width the first and second transverse longer bandage arms 110(1-2) provides less adhesive area so the hybrid choking proof bandage 105 while providing sufficient stickiness it is easy on the skin of a baby with only half the adhesive area.

The hybrid choking proof bandage 105 includes the first and second transverse longer bandage arms 110(1-2) of a first length 130(1-2) and the third and fourth shorter bandage arms 115(1-2) of a second length 135(1-2) such that the first length 130(1-2) and the second length 135(1-2) may be different. For example, the first length 130(1-2) may be more than the second length 135(1-2) such it can be about double the second length 135(1-2). The hybrid choking proof bandage 105 includes the first and second transverse longer bandage arms 110(1-2) of the first width 120 and the third and fourth shorter bandage arms 115(1-2) of the second width 125 such that the first width 120 and the second width 125 may be different and the hybrid choking proof bandage 105 includes the first and second transverse longer bandage arms 110(1-2) of the first length 130(1-2) and the third and fourth shorter bandage arms 115(1-2) of the second length 135(1-2) such that the first length 130(1-2) and the second length 135(1-2) may be different.

Figure 1C:
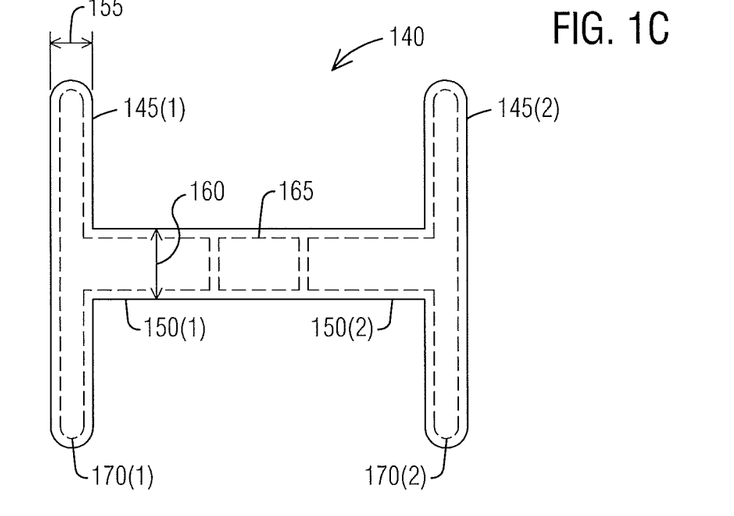
FIG. 1C illustrates a front view of a peel-resistant choking proof bandage including a first and a second transverse edge bandage arms in accordance with an exemplary embodiment of the present invention.

FIG. 1C illustrates a front view of a peel-resistant choking proof bandage 140 including a first and a second transverse edge bandage arms 145(1-2) in accordance with an exemplary embodiment of the present invention. The peel-resistant choking proof bandage 140 includes a third and a fourth standard bandage anus 150(1-2). The first and second transverse edge bandage arms 145(1-2) may have a first width 155 and the third and fourth standard bandage arms 150(1-2) may have a second width 160 such that the first width 155 and the second width 160 may be different. In other embodiments, for example, the first width 155 may be less such as about half the second width 160. The first and second transverse edge bandage arms 145(1-2) may make the peel-resistant choking proof bandage 140 peel-resistant by having a longer length to peel off on corners. The peel-resistant choking proof bandage may 140 include a medicated pad 165 in a middle portion of the peel-resistant choking proof bandage 140. The peel-resistant choking proof bandage may 140 include a first and a second sticky portions 170(1-2).

The first and second transverse edge bandage alms 145(1-2) are transverse (e.g., angled at about 90 degrees) to the third and the fourth standard bandage arms 150(1-2) and are respectively at distal ends of the third and the fourth standard bandage arms 150(1-2). The medicated pad 165 is located at about center of the third and the fourth standard bandage arms 150(1-2). The first and second transverse edge bandage arms 145(1-2) respectively includes a corresponding first sticky portion and a corresponding second sticky portion. The third and the fourth standard bandage arms 150(1-2) respectively includes a corresponding third sticky portion and a corresponding fourth sticky portion. The first and the second sticky portions 170(1-2) shows these four sticky portions in combined areas for ease of illustration.

Figure 1D:
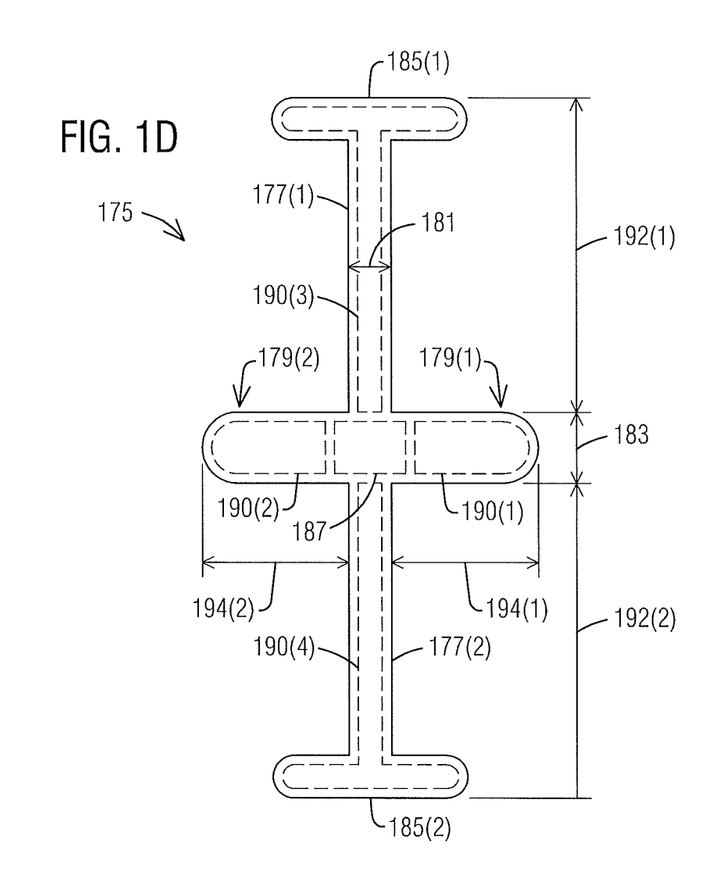
FIG. 1D illustrates a front view of another peel-resistant choking proof bandage including a first and a second transverse bandage arms in accordance with an exemplary embodiment of the present invention.

FIG. 1D illustrates a front view of another peel-resistant choking proof bandage 175 including a first and a second transverse bandage arms 177(1-2) in accordance with an exemplary embodiment of the present invention. The peel-resistant choking proof bandage 175 includes a third and a fourth standard bandage arms 179(1-2). The first and second transverse bandage arms 177(1-2) may have a first width 181 and the third and fourth standard bandage arms 179(1-2) may have a second width 183 such that the first width 181 and the second width 183 may be different. In other embodiments, for example, the first width 181 may be less such as about half the second width 183. The peel-resistant choking proof bandage 175 may include a fifth and a sixth transverse edge bandage arms 185(1-2) that may make the peel-resistant choking proof bandage 175 peel-resistant by having a longer length to peel off on corners.

The peel-resistant choking proof bandage may 175 include a medicated pad 187 in a middle portion of the peel-resistant choking proof bandage 175. The peel-resistant choking proof bandage may 175 include a plurality of sticky portions 190(1-4).

The first and second transverse bandage arms 177(1-2) may have a first length 192(1-2) each. The third and fourth standard bandage arms 179(1-2) may have a second length 194(1-2) each. The first length 192(1-2) may be greater than the second length 194(1-2). For example, the first length 192(1-2) may be twice the second length 194(1-2) or more than twice the second length 194(1-2).

Figure 2:
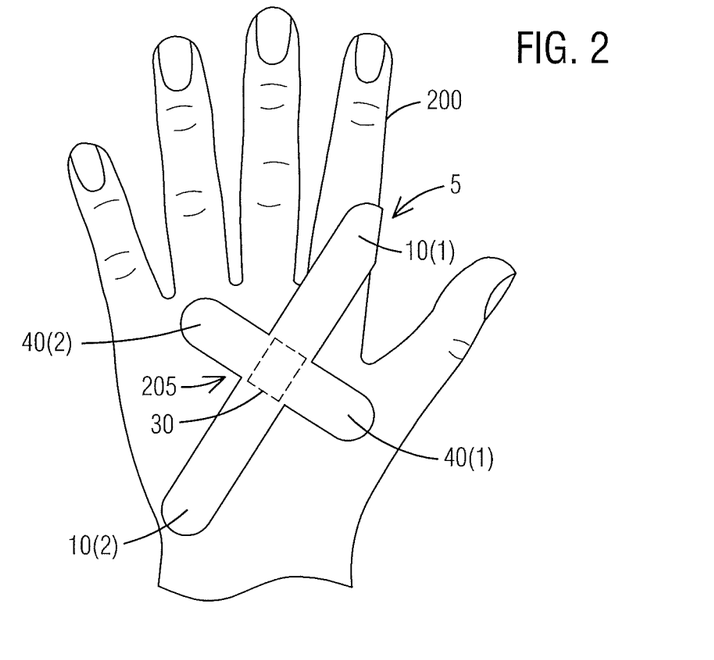
FIG. 2 illustrates a perspective view of the choking proof bandage of FIG. 1 in use on a finger according to one embodiment of the present invention.

FIG. 2 illustrates a perspective view of the first choking proof bandage 5 of FIG. 1 in use on a finger 200 according to one embodiment of the present invention. The first and second bandage arms 10(1-2) form a fork 205 which provides an extra grip on the finger 200 from the first and second sticky portions 35(1-2). The additional adhesion provided by the fork 205 makes it next to impossible for a baby to peel off the first choking proof bandage 5 from the finger 200. Having the first length 20(1-2) to be about twice the second length 25(1-2) or more than twice the second length 25(1-2) enables the forming of the fork 205. This fork design substantially mitigates the risk of choking from the first choking proof bandage 5 if not eliminates it, saving lives of babies.

Figure 3:
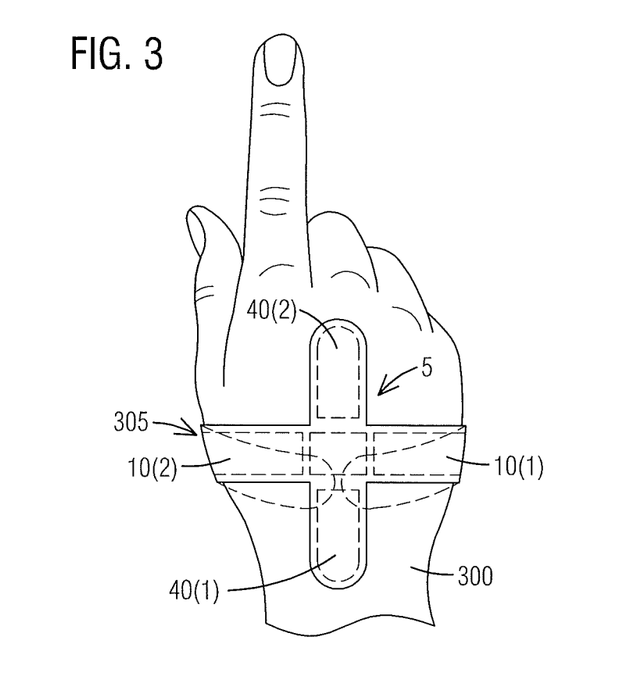
FIG. 3 illustrates a perspective view of the choking proof bandage of FIG. 1 in use on an arm according to one embodiment of the present invention.

FIG. 3 illustrates a perspective view of the first choking proof bandage 5 of FIG. 1 in use on an arm 300 according to one embodiment of the present invention. The first and second bandage arms 10(1-2) form a ring 305 which provides an extra grip on the arm 300 from the first and second sticky portions 35(1-2). The additional adhesion provided by the ring 305 makes it next to impossible for a baby to peel off the first choking proof bandage 5 from the arm 300. Having the first length 20(1-2) to be about twice the second length 25(1-2) or more than twice the second length 25(1-2) enables the forming of the ring 305. This ring design substantially mitigates the risk of choking from the first choking proof bandage 5 if not eliminates it, saving lives of babies.

An adhesive bandage is provided to cover the vaccination spot on the arm or thigh of a baby. Babies of certain age are known to peel off the bandage and chew it so the bandage becomes a choking hazard. An adhesive bandage to provide a bandage that cannot pose a choking hazard to babies.

In one embodiment, the new bandage includes an adhesive strip and a clip such that the adhesive strip is looped through the clip. The clip is shaped like a plastic hair band which is resilient in nature thus provides resistance to its removal from head. Since this clip snaps on the arm or thigh it makes difficult to remove the strip when it is peeled-off the skin of the baby by the baby. This essentially significantly mitigates the risk of choking.

In another embodiment, the new bandage includes an adhesive strip and a Velcro strap such that the adhesive strip is looped through the Velcro strap. A clip or a Velcro strap is attached to the adhesive strip to make it very difficult to remove the bandage from the arm or the thigh by ab baby. This new design of the bandage essentially significantly mitigates the risk of choking.

Figure 4:
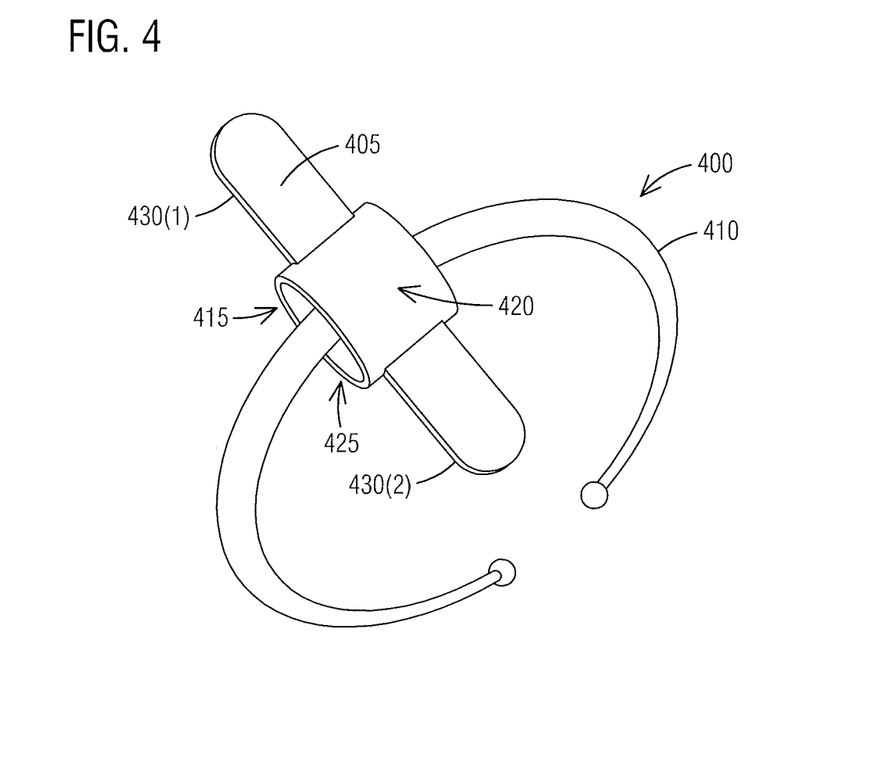
FIG. 4 illustrates a perspective view of a choking proof bandage including a strip and a clip threaded through the strip according to one embodiment of the present invention.

FIG. 4 illustrates a perspective view of a second choking proof bandage 400 including a bandage strip 405 and a clip 410 threaded through the bandage strip 405 according to another embodiment of the present invention. The bandage strip 405 includes a channel 415 in a middle portion 420 to thread through an object. The clip 410 is threaded through the channel 415 of the bandage strip 405. The clip 410 is configured to be placed on an arm or a thigh of a baby.

The second choking proof bandage 400 further includes a medicated pad 425 at an intersection of the middle portion 420 of the bandage strip 405 and the clip 410. The bandage strip 405 respectively includes a corresponding first sticky portion 430(1) and a corresponding second sticky portion 430(2). The first and second sticky portions 430(1-2) cover an area other than the medicated pad 425 and comprise an adhesive sheet. The first and second sticky portions 430(1-2) may include peel strips (not shown) to preserve the adhesion surface prior to application of the second choking proof bandage 400 on a skin of a baby.

The bandage strip 405 may be a flexible sheet of material which is sticky on one side with the medicated pad 425 stuck to the sticky side as a non-sticky and absorbent patch. The bandage strip 405 may be a woven strip of material with the medicated pad 425 including a Telfa absorbent barrier to prevent adhering to wounds.

Figure 5:
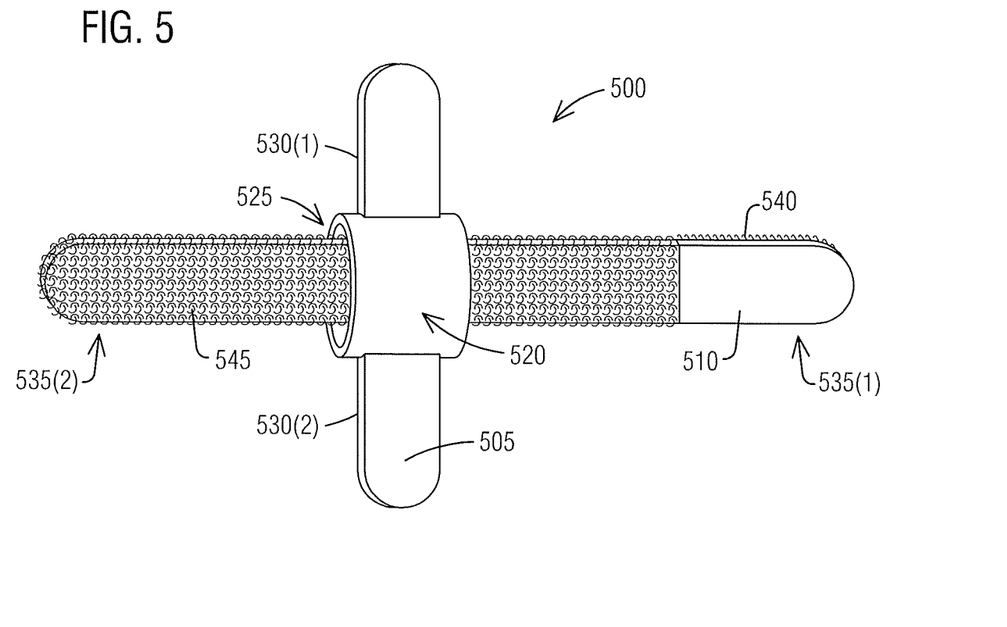
FIG. 5 illustrates a perspective view of a choking proof bandage including a strip and a Velcro band threaded through the strip according to one embodiment of the present invention.

FIG. 5 illustrates a perspective view of a third choking proof bandage 500 including a bandage strip 505 and a Velcro band 510 threaded through the bondage strip 505 according to one embodiment of the present invention. The bandage strip 505 includes a channel 515 in a middle portion 520 to thread through an object. The Velcro band 510 is threaded through the channel 515 of the bandage strip 505. The Velcro band 510 is configured to be placed on an arm or a thigh of a baby.

The third choking proof bandage 500 further comprises a medicated pad 525 at an intersection of the middle portion 520 of the bandage strip 505 and the Velcro band 510. The bandage strip 505 respectively includes a corresponding first sticky portion 530(1) and a corresponding second sticky portion 530(2). The first and second sticky portions 530(1-2) cover an area other than the medicated pad 525 and comprise an adhesive sheet. The first and second sticky portions 530(1-2) may include peel strips (not shown) to preserve the adhesion surface prior to application of the third choking proof bandage 500 on a skin of a baby. The bandage strip 505 is a flexible sheet of material which is sticky on one side with the medicated pad 525 stuck to the sticky side as a non-sticky and absorbent patch.

The Velcro band has first and second ends 535(1-2). The first end includes a plurality of Velcro hooks 540 and the second end includes a plurality of Velcro loop fasteners 545.

While embodiments of the present invention have been disclosed in exemplary foul's, it will be apparent to those skilled in the art that many modifications, additions, and deletions can be made therein without departing from the spirit and scope of the invention and its equivalents, as set forth in the following claims.

Embodiments and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure embodiments in detail. It should be understood, however, that the detailed description and the specific examples, while indicating preferred embodiments, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms.

In the foregoing specification, the invention has been described with reference to specific embodiments. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of invention.

Although the invention has been described with respect to specific embodiments thereof, these embodiments are merely illustrative, and not restrictive of the invention. The description herein of illustrated embodiments of the invention is not intended to be exhaustive or to limit the invention to the precise forms disclosed herein (and in particular, the inclusion of any particular embodiment, feature or function is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Respective appearances of the phrases "in one embodiment," "in an embodiment," or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Although the steps, operations, or computations may be presented in a specific order, this order may be changed in different embodiments. In some embodiments, to the extent multiple steps are shown as sequential in this specification, some combination of such steps in alternative embodiments may be performed at the same time.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It will also be appreciated that one or more of the elements depicted in the drawings/figures can also be implemented in a more separated or integrated manner, or even removed or rendered as inoperable in certain cases, as is useful in accordance with a particular application.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

What is claimed is:

1. An adhesive bandage, comprising:
   a first and a second bandage arms;
   a third and a fourth bandage arms, wherein the first and second bandage arms are transverse to the third and fourth bandage arms and wherein the first and second bandage arms are longer in length than the third and fourth bandage arms;
   a medicated pad at an intersection of the first and second bandage arms and the third and fourth bandage arms;
   a fifth transverse edge bandage arm located at an end of the first bandage arm and configured to provide a longer length to peel off on a first corner; and
   a sixth transverse edge bandage arm located at an end of the second bandage arm and configured to provide a longer length to peel off on a second corner.

2. The adhesive bandage of claim 1, wherein the first and second bandage arms respectively includes a corresponding first sticky portion and a corresponding second sticky portion.

3. The adhesive bandage of claim 2, wherein the third and fourth bandage arms respectively includes a corresponding third sticky portion and a corresponding fourth sticky portion.

4. The adhesive bandage of claim 3, wherein the first and second sticky portions and the third and fourth sticky portions cover an area other than the medicated pad and comprise an adhesive sheet.

5. The adhesive bandage of claim 4, wherein the adhesive bandage is configured for placing on a skin after blood tests or vaccinations.

6. The adhesive bandage of claim 1, wherein the adhesive bandage is a flexible sheet of material which is sticky on one side with the medicated pad stuck to the sticky side as a non-sticky and absorbent patch.

7. The adhesive bandage of claim 6, wherein the adhesive bandage is a woven strip of material with the medicated pad including an absorbent barrier to prevent adhering to wounds.

8. The adhesive bandage of claim 1, wherein the first and second bandage arms having a first length each and the third and fourth bandage arms having a second length each such that the first length is greater than the second length.

9. The adhesive bandage of claim 8, wherein the first length is about twice or more than twice the second length.

10. The adhesive bandage of claim 1, wherein the first and second bandage arms are transverse to the third and fourth bandage arms at about 90 degrees or even less at about 85 degrees or even lesser at about 60 degrees.

* * * * *